(12) United States Patent
Kappler

(10) Patent No.: US 8,373,135 B2
(45) Date of Patent: Feb. 12, 2013

(54) COUNTING DETECTOR AND COMPUTED TOMOGRAPHY SYSTEM

(75) Inventor: Steffen Kappler, Effeltrich (DE)

(73) Assignee: Siemens Aktiengesellschaft, Munich (DE)

( * ) Notice: Subject to any disclaimer, the term of this patent is extended or adjusted under 35 U.S.C. 154(b) by 42 days.

(21) Appl. No.: 13/164,892

(22) Filed: Jun. 21, 2011

(65) Prior Publication Data

US 2011/0311022 A1    Dec. 22, 2011

(30) Foreign Application Priority Data

Jun. 22, 2010   (DE) .......................... 10 2010 024 626

(51) Int. Cl.
  *G01T 1/24*   (2006.01)
  *G01T 1/20*   (2006.01)
(52) U.S. Cl. ................ 250/370.09; 250/336.1; 250/369; 250/370.01
(58) Field of Classification Search .............. 250/370.09
    See application file for complete search history.

(56) References Cited

U.S. PATENT DOCUMENTS

| | | | |
|---|---|---|---|
| 6,809,311 B2 | 10/2004 | Burckhardt | |
| 7,208,739 B1 * | 4/2007 | Yanoff et al. | 250/363.09 |
| 7,983,397 B2 | 7/2011 | Michel et al. | |
| 2002/0179844 A1 * | 12/2002 | Lundqvist | 250/371 |
| 2011/0051901 A1 | 3/2011 | Michel et al. | |

FOREIGN PATENT DOCUMENTS

DE    102006006411 A1    8/2007

OTHER PUBLICATIONS

German priority application No. DE 10 2010 024 626.3 filed on Jun. 22, 2010 and not yet published.

* cited by examiner

*Primary Examiner* — Marcus Taningco
(74) *Attorney, Agent, or Firm* — Harness, Dickey & Pierce, P.L.C.

(57) ABSTRACT

A counting detector is disclosed. In at least one embodiment, the counting detector includes sensors for converting radiation quanta into electrical pulses and an evaluation unit with a number of energy thresholds, wherein the evaluation unit generates for each sensor a count value for each energy threshold from the pulses, which count value represents the number of radiation quanta with an energy above the respective energy threshold. In at least one embodiment, one of the energy thresholds is arranged directly above a characteristic energy of radiation quanta causing double counting in order to correct double counting; and a correction unit calculates a corrected count value from the count values of the energy thresholds, which corrected count value has reduced double counting for at least one of the energy thresholds. Images with an improved contrast-to-noise ratio and, at the same time, a reduced X-ray dose can be generated on the basis of the at least one corrected count value. In at least one embodiment, the invention moreover relates to a computed tomography system with such a counting detector.

18 Claims, 3 Drawing Sheets

COUNTING DETECTOR AND COMPUTED TOMOGRAPHY SYSTEM

PRIORITY STATEMENT

The present application hereby claims priority under 35 U.S.C. §119 on German patent application number DE 10 2010 024 626.3 filed Jun. 22, 2010, the entire contents of which are hereby incorporated herein by reference.

FIELD

At least one embodiment of the invention generally relates to a counting detector, which includes sensors for converting radiation quanta into electrical pulses and an evaluation unit with a number of energy thresholds. At least one embodiment of the invention moreover generally relates to a computed tomography system with such a counting detector.

BACKGROUND

Until now, use has mainly been made of integrating detectors for detecting gamma and X-ray radiation, which detectors generate an electrical signal proportional to the intensity of incident X-ray radiation over a given time interval. In the process, the detectors are structured into individual sensors for spatially-resolved acquisition of the radiation. By way of example, such detectors are used in computed tomography systems. In such systems, X-ray projections of an examination region of a patient are acquired from many different projection directions by way of the detector, and slice or 3D images are calculated therefrom according to known reconstruction methods.

A development of these systems resides in the use of so-called counting detectors. These allow separate acquisition of absorption events for each individual radiation quantum. The counting and energy-selective acquisition more particularly allows the evaluation of material-specific properties of the examination region with, at the same time, a reduced X-ray dose; this can be converted into increased contrast in the reconstructed image.

Use can be made of both direct-conversion and optically counting detectors. In the case of direct-conversion detectors, the X-ray quanta are directly converted into free charge carriers in a semiconductor layer as a result of interaction processes with a semiconductor material, which charge carriers are accelerated in an electric field between two electrodes arranged opposite one another. CdTe, CdZnTe, CdTeSe or CdZnTeSe semiconductor materials can for example be used as semiconductor material. The charge carrier transport induces currents on the electrodes, which can be registered as an electrical pulse. By contrast, in the case of optically converting detectors, the conversion occurs in two stages. In a first stage the X-ray quantum is converted into light pulses by means of a scintillator with a short decay time, for example by means of a BGO, LSO, or CuI scintillator. The light signal thus generated is converted into an electrical pulse in a second stage in a photodiode that is optically coupled to the scintillator. In both cases, the electrical pulse thus generated has a pulse height that is characteristic for the energy of the incident X-ray quantum.

The pulses are subsequently routed to an evaluation unit for subsequent processing. There, for each sensor, a count value is generated for at least one energy threshold, which count value represents the number of X-ray quanta above the respective energy threshold. In the process, the count is performed by means of a count circuit (trigger circuit), which for a generated pulse increments the count value for the energy threshold when a pulse threshold corresponding to the respective energy threshold is exceeded. In the case of simple, conventional CT imaging only one energy threshold is required and it typically lies in a range between 15 keV and 35 keV. A further threshold, for example in the range between 50 keV and 80 keV, is provided for dual-energy imaging or optimized conventional CT imaging.

However, count values can be influenced by absorption events of X-ray quanta in adjacently arranged sensors and hence they can be falsified. By way of example, in the case of a so-called K-escape effect, part of the energy of an X-ray quantum is carried into the neighboring sensor by fluorescence effects. Moreover, if an X-ray quantum is converted in the vicinity of the sensor edge, the resulting signal may be distributed to locally adjacent sensors. This effect is also referred to as charge sharing or, even better, energy splitting. Both effects often result in double counting of individual X-ray quanta if the energy threshold is low compared to the energy of the primary X-ray quantum. Secondly, count values in respect of relatively high energy thresholds, which are exceeded by the energy of the primary X-ray quantum in the case of complete conversion, are underestimated.

In the field of human medicine, one is moreover confronted with relatively high quantum flux rates of e.g. more than $10^8$ X-ray quanta/mm$^2$*s. Separation of X-ray quanta, which are successively incident over time, on the basis of the registered signals can therefore only be ensured if the sensor areas are reduced in size, for example to less than 0.1 mm$^2$. However, in most converter materials this is connected with a significant increase in the K-escape effect and energy splitting. Double counting of individual X-ray quanta at lower energy thresholds and the loss of count events at correspondingly higher energy thresholds have a negative effect on the image contrast and the image noise.

Hence, it is an object of the present invention to develop a counting detector and a computed tomography system with such a detector such that a negative effect on the image quality resulting from double counting of individual X-ray quanta is at least markedly reduced.

SUMMARY

At least one embodiment is directed to a counting detector and at least one embodiment is directed to a computed tomography system. Advantageous developments are the subject matter of the dependent claims.

At least one embodiment of the invention proceeds from the discovery that the known coincidence circuits for correcting double counting only operate reliably for low-flux applications and are not suitable for the high flux rates, as occur in human medical applications. In this circuit, adjacent sensors are in a coincidence circuit via a comparator, and so count values or electrical signals of the sensors incident within a certain time interval are registered and combined to a resulting signal for the incident X-ray quantum. However, these circuits have a complex design and can only be implemented with a limited clock rate, and so X-ray quanta incident in quick succession cannot be resolved in time. An alternative to this circuit consists of selecting an energy threshold beyond the typical pulse heights of K-escape X-ray quanta or fragments of the electrical pulse from energy splitting. Although the count values for the energy thresholds do not contain double counting in this case, this advantage is at the cost of a reduction in the spectral sensitivity and a loss of dose because absorption events of such low-energy X-ray quanta can no longer be registered at all and hence cannot contribute to imaging.

The inventor has discovered that the introduction of at least one additional energy threshold and a subsequent calculation with all count values from a sensor allows the image quality to be significantly increased.

Hence, according to at least one embodiment of the invention, a counting detector is proposed, which has sensors for converting radiation quanta into electrical pulses and an evaluation unit with a number of energy thresholds, wherein the evaluation unit generates for each sensor a count value for each energy threshold from the pulses, which count value represents the number of radiation quanta with an energy above the respective energy threshold, wherein one of the energy thresholds is arranged directly above a characteristic energy of radiation quanta causing double counting in order to correct double counting, and wherein a correction unit calculates a corrected count value from the count values of the energy thresholds, which corrected count value has reduced double counting for at least one of the energy thresholds.

The energy threshold used for correcting double counting is for example set directly above the energy of K-escape X-ray quanta. Hence, the position of this threshold in particular depends on the material properties of the converter. Likewise, it would be feasible to set the energy threshold directly above a characteristic energy registered in respect of fragments of an electrical signal generated by an X-ray quantum. However, use can also be made of a combination of two or more of such energy thresholds.

Hence, according to at least one embodiment of the invention, at least one count value can be generated at the lowest energy threshold that is not falsified by double counting of the type considered. Thus, as a result, the energy range covered by the energy thresholds is subdivided into segments, wherein the effect of double counting of a considered type is particularly high in one energy segment and particularly low in a second energy segment. In other words, this means that difference energy ranges can be imaged, in which double counting occurs with a very high or very low probability. By performing calculations on the count values for at least some of the energy thresholds, it is possible to calculate a corrected count value with reduced double counting for at least one of the energy thresholds if the statistical distribution of the various absorption events are known in the difference energy ranges. This corrected count value depends, inter alia, on the spectral distribution of the incident X-ray radiation, the converter material, and the dimensions of the sensor. The relative position of the thresholds and the specific calculation of the count values can be determined by an optimization, for example on the basis of a Monte Carlo simulation. Image value criteria can for example be the image noise, iodine-water or dual-energy contrast-to-noise ratios.

A suitable calculation can reduce the negative effect of double counting. At the same time, the dose input from the original radiation quanta from the difference energy range can be used, at least in part. This results in an improved contrast reproduction and, in particular, a reduction in the image noise in the case of an unchanging patient dose.

Moreover, calculations are only performed on count values from a single sensor. Coincidence circuits are no longer required. In particular, this ensures processing in real-time conditions, even in the case of high-flux applications, as are present in the field of human medicine.

The corrected count values for energy thresholds from the low energy range below the correction threshold are reduced by count signals from double counting, while the corrected count values for energy thresholds from the upper energy range above the correction threshold are increased by the number of X-ray quanta with energy loss as a result of crosstalk to an adjacent sensor. In this context, a correction threshold should be understood to mean that energy threshold that is used for correcting double counting.

The electrical pulses preferably have a pulse height that is characteristic for the energy of the respective energy quantum. By way of example, the count values are generated in the process by way of a trigger circuit, which increments the count value for the energy threshold when a pulse threshold corresponding to the respective energy threshold is exceeded. By way of example, pulses of this type are generated by a direct-conversion converter. They can be converted into count signals by means of a trigger circuit, which can be implemented easily.

In a simple case, the correction unit is configured for weighted summation of the count values, each of which having a weighting specific to the energy threshold. This type of calculation allows a particularly effective reduction in the negative effect of double counting with, at the same time, low calculation resources.

For the purpose of a material-specific examination, a first energy threshold is, in an advantageous embodiment of the invention, arranged below and a second energy threshold is arranged above the energy threshold used for the purpose of correction.

At least one of the energy thresholds and/or at least one of the specific weightings are advantageously selected depending on an imaging application. The in part very different medical questions and targets in the imaging applications require the individual examinations to be carried out with different X-ray spectra and X-ray flux rates. This can have significant effects on the double-counting effects, more particularly on the position of the energy ranges in which double counting is observed. Hence, in order to correct the count values, it is necessary to prescribe the energy thresholds and/or the specific weightings depending on the imaging application in order to obtain an optimal result. By way of example, this can be brought about in an automated fashion in conjunction with the selection of specific examination protocols before the examination starts.

In the case of a CT system with a conventional X-ray tube (tungsten anode, 120 kV tube voltage) and a CdTe-based, quanta counting detector, the following was discovered: images in contrast-agent examinations of typical anatomies have a particularly high contrast-to-noise ratio if the first energy threshold is arranged at 20 keV, the second energy threshold is arranged at 70 keV, and the energy threshold for correcting double counting is arranged at 35 keV. It goes without saying that the positions of the first and the second energy thresholds can vary within a certain range and have an almost identical achievable result. Variations in the positions are therefore also included in at least one embodiment of the invention.

Correcting double counting whilst at the same time utilizing the dose from the energy range up to the correction threshold can be achieved particularly well in this case if the weighting for the count value of the first energy threshold is 0.53, the weighting for the count value of the second energy threshold is −0.26, and the weighting for the count value of the energy threshold for correcting double counting is 0.73. It goes without saying that the specific weighting can also be varied within a certain range without having a significant adverse effect on the achievable result.

Furthermore one of the energy thresholds for correcting double counting is advantageously arranged directly below the characteristic energy of radiation quanta causing double counting. By way of example, depending on the spectral characteristic of a direct-conversion converter, an additional count value is arranged with an energy threshold directly below the characteristic energy of the K-escape X-ray quanta. The count values of the two correction thresholds are strongly correlated statistically. The count value of the lower energy threshold in this case contains additional multiple countings of high-energy radiation quanta, from which K-escape X-ray quanta emerge through interaction processes, and count signal from original radiation quanta from the difference energy range.

As already described above, the counting detector is a direct-conversion detector, with the sensors each having a directly converting semiconductor layer.

As an alternative thereto, the counting detector can advantageously be an indirect-conversion detector, with the sensors having a scintillator with a downstream photodiode.

A second aspect of at least one embodiment of the invention relates to a computed tomography system with an above-described counting detector.

BRIEF DESCRIPTION OF THE DRAWINGS

In the following text, the invention will be explained in more detail on the basis of example embodiments and on the basis of drawings, in which.

Figure 1:
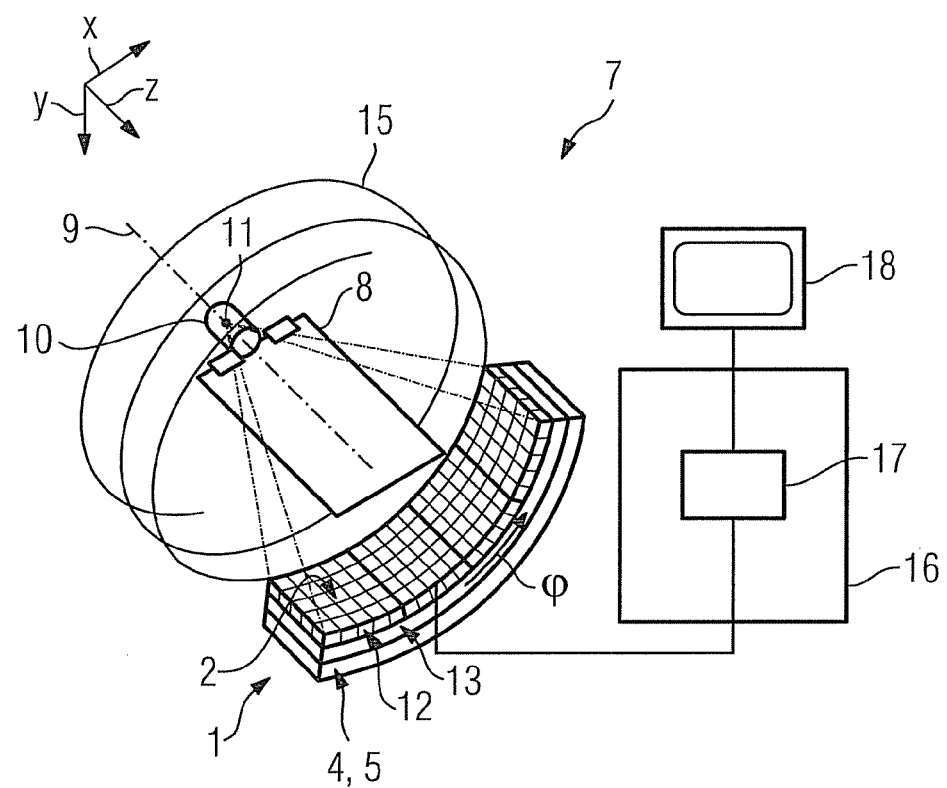
FIG. 1 shows a computed tomography system with a counting detector according to an embodiment of the invention.

In the figures, equivalent or functionally equivalent elements have been denoted by the same reference sign. In the case of repeating elements within one figure, only one element has in each case been provided with a reference sign for reasons of clarity. The illustrations in the figures are schematic and not necessarily true to scale, wherein scales may vary between the figures.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted, in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The counting detector 1 according to an embodiment of the invention can be used in conjunction with different imaging modalities, for example in conjunction with CT, C-arm, PET, or SPECT scanners. Here, in an example fashion, FIG. 1 shows a computed tomography system 7 with a counting detector 1 according to an embodiment of the invention.

The computed tomography system 7 comprises a patient support table 8 for supporting a patient to be examined. It furthermore comprises a gantry (not illustrated) with a recording system 1, 10 mounted such that it can rotate about a system axis 9. The recording system 1, 10 has an X-ray tube 10 and the counting detector 1 according to the invention, which is illustrated in more detail in FIG. 2; here, X-ray tube and counting detector are aligned opposite one another such that X-ray radiation emitted by the focus 11 of the X-ray tube 10 during operation impinges on the detector 1. A collimator 12 is placed in front of the detector to suppress the scattered radiation created in the patient; said collimator only passes to the detector 1 the primary radiation that was emitted by the focus 11 and attenuated as a function of the patient penetration.

In principle, both an indirect-conversion, i.e. optically counting, detector and a direct-conversion detector can be used as a counting detector 1. In this example, a direct-conversion detector 1 is integrated with a semiconductor layer 13 on the basis of a CdTe semiconductor material. However, use can for example also be made of CdZnTe—, CdTeSe—, or CdZnTeSe-based semiconductor materials. In the semiconductor layer 13, the incident X-ray quanta are converted into free charge carriers, registered as electrical signals 14 by way of downstream readout electronics as a result of a forced charge carrier transport in an electrical field, and converted into an electrical pulse 3, which is evaluated by way of an evaluation unit 4. The detector 1 is subdivided into individual sensors 2 or pixels for spatially-resolved acquisition of the absorption events.

In order to record an image of an examination region, projections are registered from a plurality of different projection directions when the recording system 1, 10 rotates about the system axis 9, wherein the detector 1 registers count values Z1, Zk, Z2 for each projection and for each sensor 2. In the case of a helical scan, there is, for example simultaneously, a continuous adjustment of the patient support table 8 in the direction of the system axis 9 during a rotation of the recording system 1, 10. In this type of scan, the X-ray tube 10 and the detector 1 therefore move along a helical path 15 around the patient. A correction unit 5 establishes at least one corrected count value Zkorr from the count values Z1, Zk, Z2 according to a method described in more detail below. The count values Z1, Zk, Z2, Zkorr are subsequently serialized in a sequencer and transmitted to an image computer 16. The image computer 16 contains a reconstruction unit 17, which reconstructs an image, e.g. in the form of a slice image of the patient, from the count values Z1, Zk, Z2, Zkorr according to a method known per se to a person skilled in the art. The image can be displayed on a display unit 18, e.g. a video monitor, connected to the image computer 16.

Figure 2:
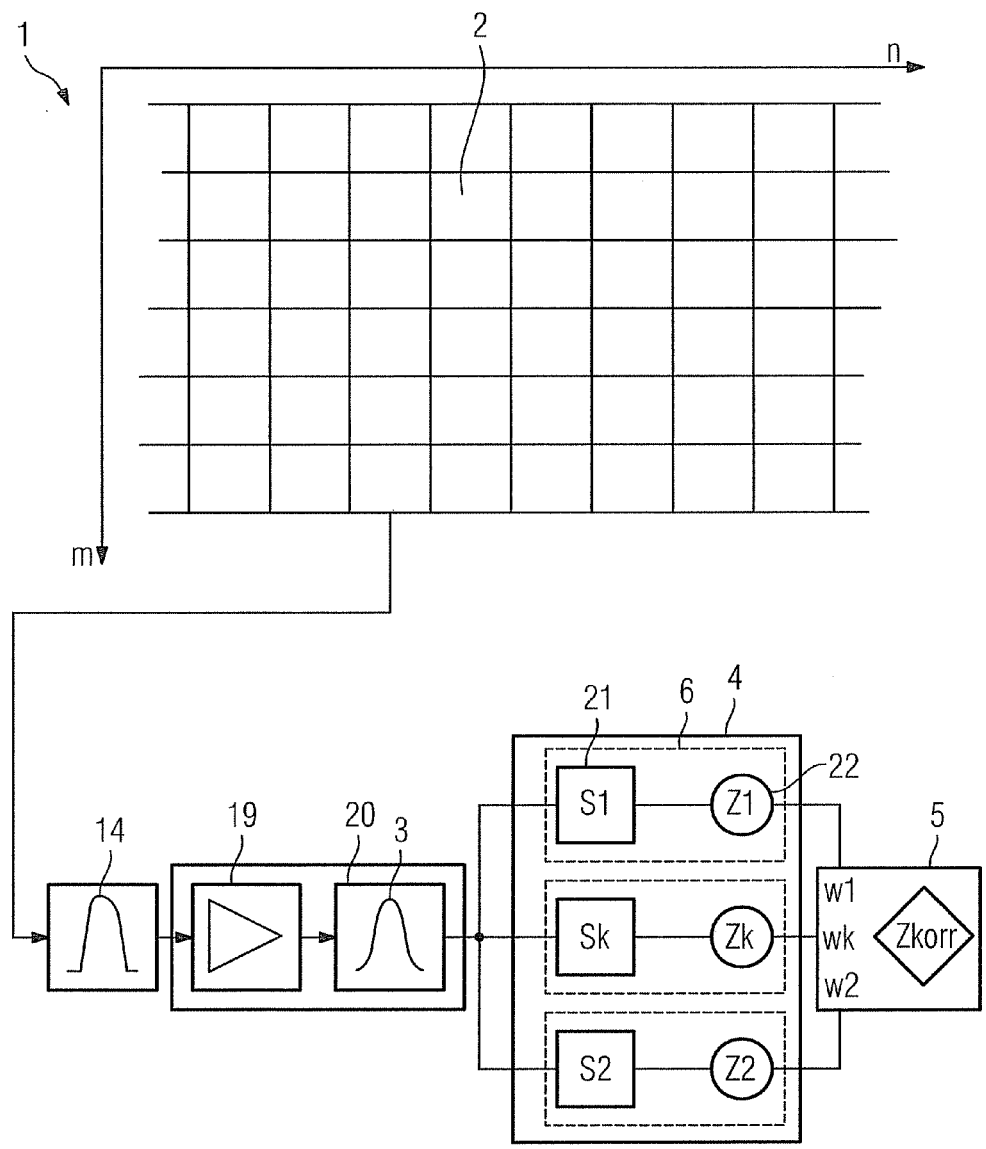
FIG. 2 shows the detector according to an embodiment of the invention with an evaluation unit.

A preferred variant of the detector 1 according to an embodiment of the invention with the evaluation unit 4 and the correction unit 5 is illustrated in FIG. 2 in a block-diagram-esque illustration. This figure shows the detector 1 with a plurality of sensors 2, arranged in an m×n-matrix-like fashion. The electrical signals 14 generated by the sensors 2 when an X-ray quantum is incident are transmitted to a preamplifier 19 with a connected signal conditioner 20. The signal conditioner 20 generates an electrical pulse 3 from the electrical signal 14, which electrical pulse has a pulse height that is characteristic for the energy of the respective radiation quantum. The pulses 3 are subsequently evaluated in an evaluation unit 4. In the process, respectively one count value Z1, Zk, Z2 is generated for a number of energy thresholds S1, Sk, S2.

As explained above, the count values Z1, Z2 are falsified by double counting if no further measures are taken; the extent of this depends on the position of the energy thresholds S1, S2. Double counting occurs, inter alfa, as a result of crosstalk of the electrical signals 14, transformed from the X-ray quanta, or K-escape X-ray quanta, generated during energy transport, in adjacently arranged sensors 2.

In order to correct the count values Z1, Z2, a further count value Zk is generated for an energy threshold Sk arranged between the energy thresholds S1, S2. The evaluation unit 4 has for each energy threshold S1, Sk, S2 a trigger circuit 6, which evaluates the pulse 3 by means of three comparators 21 connected in parallel. The comparator 21 generates a count signal when a pulse threshold corresponding to the respective energy threshold S1, Sk, S2 is exceeded and this count signal increments the count value in a counter 22 connected to the respective comparator 21. The two outer energy thresholds S1, S2 are selected depending on the materials to be examined in the patient, while the middle energy threshold Sk serves as a correction threshold and is set depending on the converter material.

In the present example embodiment, the two outer energy thresholds S1, S2 for a contrast-agent examination are set to 20 keV and 70 keV. The middle energy threshold Sk lies at 35 keV and therefore just above the energy of K-escape X-ray quanta in CdTe semiconductor material.

A correction unit 5 is designed such that a corrected count value Zkorr with reduced double counting is calculated for at least one of the energy thresholds S1, Sk, S2 from the count values Z1, Zk, Z2 of the energy thresholds S1, Sk, S2. Hence, the count values Z1, Zk, Z2 for the individual energy thresholds S1, Sk, S2 are added in a weighted fashion. The factors w1=0.53, wk=0.73, and w2=−0.26 were established as suitable weightings for a direct-conversion converter based on CdTe and energy thresholds at S1=20 keV, Sk=35 keV, and S2=70 keV. Hence, the corrected count value is accordingly calculated according to the following formula:

$$Zkorr = w1 \cdot Z1 + wk \cdot Zk + w2 \cdot Z2, \text{ with}$$

Zkorr:=corrected count value,
Z1=count value for the first energy threshold S1,
Zk=count value for the energy threshold for a correction Sk,
Z2=count value for the second energy threshold S2,
w1=weighting for the first energy threshold S1,
wk=weighting for the energy threshold for a correction Sk,
w2=weighting for the second energy threshold S2,
and with the following boundary conditions:

$$w1 = 1 - wk - w2,$$

$$wk, w2 \in (-\infty, \infty).$$

The count values established thus allow the calculation of slice and volume images with an improved contrast-to-noise ratio at, at the same time, a lower X-ray dose.

It should be mentioned that the position of the energy thresholds S1, Sk, S2 and the suitable weightings w1, wk, w2 depend, in particular, on the medical question and physical boundary conditions, more particularly on the dimensions of the sensors 2, the converter material, and the X-ray spectrum used. Suitable values can be established in the run-up to an examination by means of a simulation, for example by way of a Monte Carlo simulation.

Figure 3:
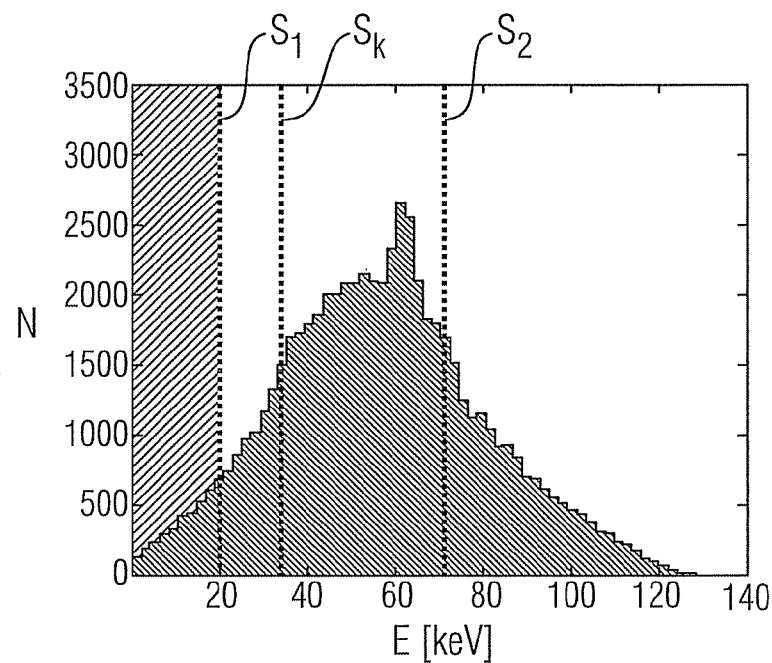
FIG. 3 shows a statistical distribution of radiation-quanta energy for a sensor.
Figure 4:
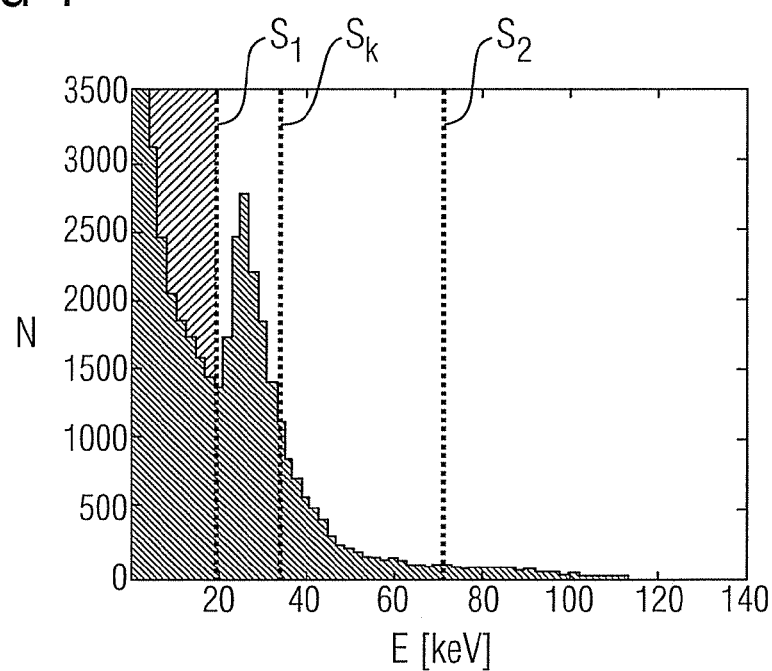
FIG. 4 shows a statistical distribution of radiation-quanta energy for a sensor that is locally adjacent to the sensor.

FIG. 3 and FIG. 4 show results of such a simulation. The simulation assumes that the sensor area is 225×225 $\mu m^2$ and the thickness of the CdTe semiconductor layer is 1.6 mm. An X-ray spectrum that was generated at 120 kV and penetrates a 20 cm thick water phantom was simulated. The x-axis represents the equivalent of an energy corresponding to the electrical pulse. The number of expected radiation-quantum events is plotted along the y-axis. FIG. 3 illustrates the expected count rates for a central sensor 2. FIG. 4 shows a situation for a sensor arranged locally adjacent to the central sensor 2. It can be identified that count rates can be observed at low energies that cause double counting in the respective sensor 2 as a result of K-escape X-ray quanta and crosstalk of the generated electrical signals. Moreover, the three energy thresholds S1, Sk, S2 for which count values Z1, Zk, Z2 are registered in a sensor 2 have been plotted in both FIGS. 3 and 4. It should be mentioned that in the case of the CdTe-based counting detector 1, the lowest energy threshold S1 at 20 keV coincides with the proposed further energy threshold for correcting double counting directly below the characteristic energy of radiation quanta from K-escape effects that cause double counting and this greatly simplifies a technical implementation of the evaluation unit.

By way of example, the position of the energy thresholds S1, Sk, S2 can emerge from an optimization of the image noise or a contrast-to-noise ratio.

The image noise emerges from the following equation:

$$\sigma korr^2 = w1^2 \sigma1^2 + wk^2 \sigma k^2 + w2^2 \sigma 2^2 + 2 \cdot w1 \cdot wk \cdot cov(Z1, Zk) + 2 \cdot w1 \cdot w2 \cdot cov(Z1, Z2) + 2 \cdot w2 \cdot wk \cdot cov(Z2, Zk),$$

with
σkorr=standard deviation of the image noise corresponding to the count value Zkorr,
σk=standard deviation of the image noise corresponding to the count value Zk of the energy threshold Sk,
σ1=standard deviation of the image noise corresponding to the count value Z1 of the energy threshold S1,
σ2=standard deviation of the image noise corresponding to the count value Z2 of the energy threshold S2,
wherein the following boundary conditions hold true:

$$w1 = 1 - wk - w2,$$

$$wk, w2 \in (-\infty, \infty),$$

and the following physical truths are utilized:

$$cov(Z1, Zk) > cov(Z1, Z2) > cov(Z2, Zk).$$

By contrast, the contrasts emerge from the following equation:

$$Ckorr = w1 \cdot C1 + wk \cdot Ck + w2 \cdot C2, \text{ with}$$

Ckorr=Contrast corresponding to the count value Zkorr,
Ck=Contrast corresponding to the count value Zk of the energy threshold Sk,
C1=Contrast corresponding to the count value Z1 of the energy threshold S1,
C2=Contrast corresponding to the count value Z2 of the energy threshold S2.

By contrast, the squared contrast-to-noise ratio emerges from:

$$CNRkorr^2 = Ckorr^2 / \sigma korr^2.$$

As a result of the additional energy threshold SK for correcting double counting and an optimized weighted calculation performed on the count values Z1, Zk, Z2 for the energy thresholds S1, Sk, S2, it is possible to increase the squared iodine-water contrast-to-noise ratio $CNR^2$ by 6%. Furthermore, the image noise is reduced by 3%, which can be converted into a reduction in the patient dose by 6%.

The following summary can be made:

An embodiment of the invention relates to a counting detector 1, which has sensors 2 for converting radiation quanta into electrical pulses 3 and an evaluation unit 4 with a number of energy thresholds S1, Sk, S2, wherein the evaluation unit 4 generates for each sensor 2 a count value Z1, Zk, Z2 for each energy threshold S1, Sk, S2 from the pulses 3, which count value represents the number of radiation quanta with an energy above the respective energy threshold S1, Sk, S2, wherein one of the energy thresholds Sk is arranged directly above a characteristic energy of radiation quanta causing double counting in order to correct double counting, and wherein a correction unit 5 calculates a corrected count value Zkorr from the count values Z1, Zk, Z2 of the energy thresholds S1, Sk, S2, which corrected count value has reduced double counting for at least one of the energy thresholds S1, Sk, S2. Images with an improved contrast-to-noise ratio and, at the same time, a reduced X-ray dose can be generated on the basis of the at least one corrected count value Zkorr. An embodiment of the invention moreover relates to a computed tomography system 7 with such a counting detector 1.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore; with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A counting detector, comprising:
    sensors to convert radiation quanta into electrical pulses;
    an evaluation unit, including a number of energy thresholds, to generate, for each of the sensors, a count value for each of the energy thresholds from the electrical pulses, each of the count values representing a number of radiation quanta with an energy above a respective one of the energy thresholds, wherein one of the energy thresholds is arranged directly above a characteristic energy of radiation quanta causing double counting in order to correct double counting; and
    a correction unit to calculate a corrected count value from the count values of the energy thresholds, the corrected count value including reduced double counting for at least one of the energy thresholds.

2. The counting detector as claimed in claim 1, wherein the electrical pulses include a pulse height that is characteristic for the energy of the respective radiation quantum and the count values are generated by way of a trigger circuit, which increments the count value for the energy threshold when a pulse threshold corresponding to the respective energy threshold is exceeded.

3. The counting detector as claimed in claim 1, wherein the correction unit performs a weighted summation of the count values, each including a weighting specific to the energy threshold.

4. The counting detector as claimed in claim 1, wherein, for the purpose of a material-specific examination, a first energy threshold is arranged below and a second energy threshold is arranged above the energy threshold used for the purpose of correction.

5. The counting detector as claimed in claim 4, wherein at least one of the following are selected depending on an imaging application:
    at least one of the energy thresholds, and
    at least one of the specific weightings.

6. The counting detector as claimed in claim 5, wherein the first of the energy thresholds is arranged at 20 keV, the second of the energy thresholds is arranged at 70 keV, and the energy threshold for correcting double counting is arranged at 35 keV.

7. The counting detector as claimed in claim 6, wherein the weighting for the count value of the first energy threshold is 0.53, the weighting for the count value of the second energy threshold is −0.26, and the weighting for the count value of the energy threshold for correcting double counting is 0.73.

8. The counting detector as claimed in claim 1, wherein one further of the energy thresholds for correcting double counting is arranged directly below the characteristic energy of radiation quanta causing double counting.

9. The counting detector as claimed in claim 1, wherein the detector is a direct-conversion detector and the sensors include a directly converting semiconductor layer.

10. The counting detector as claimed in claim 1, wherein the detector is an indirect-conversion detector and the sensors include a scintillator with a downstream photodiode.

11. A computed tomography system comprising a counting detector as claimed in claim 1.

12. The counting detector as claimed in claim 2, wherein the correction unit performs a weighted summation of the count values, each including a weighting specific to the energy threshold.

13. The counting detector as claimed in claim 2, wherein, for the purpose of a material-specific examination, a first energy threshold is arranged below and a second energy threshold is arranged above the energy threshold used for the purpose of correction.

14. The counting detector as claimed in claim 3, wherein at least one of the following are selected depending on an imaging application:
    at least one of the energy thresholds, and
    at least one of the specific weightings.

15. The counting detector as claimed in claim 12, wherein at least one of the following are selected depending on an imaging application:
    at least one of the energy thresholds, and
    at least one of the specific weightings.

16. The counting detector as claimed in claim 13, wherein at least one of the following are selected depending on an imaging application:
    at least one of the energy thresholds, and
    at least one of the specific weightings.

17. The counting detector as claimed in claim 5, wherein the weighting for the count value of the first energy threshold is 0.53, the weighting for the count value of the second energy threshold is −0.26, and the weighting for the count value of the energy threshold for correcting double counting is 0.73.

18. A computed tomography system comprising a counting detector as claimed in claim 2.

* * * * *